United States Patent [19]
Landau

[11] Patent Number: 6,096,002
[45] Date of Patent: Aug. 1, 2000

[54] NGAS POWERED SELF-RESETTING NEEDLE-LESS HYPODERMIC JET INJECTION APPARATUS AND METHOD

[75] Inventor: Sergio Landau, Laguna Nigel, Calif.

[73] Assignee: Bioject, Inc., Portland, Oreg.

[21] Appl. No.: 09/195,334

[22] Filed: Nov. 18, 1998

[51] Int. Cl.[7] .............................. A61M 5/30; A61M 37/00
[52] U.S. Cl. ................... 604/68; 604/69; 604/143
[58] Field of Search ................... 604/68, 69, 70, 604/71, 131, 140, 141, 143

[56] References Cited

U.S. PATENT DOCUMENTS

| | | | |
|---|---|---|---|
| 3,688,765 | 9/1972 | Gasaway | 128/173 H |
| 5,503,627 | 4/1996 | McKinnon et al. | 604/72 |
| 5,865,795 | 2/1999 | Schiff et al. | 604/70 |

Primary Examiner—Glenn K. Dawson
Assistant Examiner—Michael Hayes
Attorney, Agent, or Firm—Terry L. Miller

[57] ABSTRACT

A needle-less hypodermic jet injection device includes a hand-held injector, and a drug injection cartridge which provides a cylinder of liquid medication to be injected, an injection orifice, and an injection piston forceful movement of which in the cylinder causes an injection jet of medication to be expelled from the orifice. The injection device also includes a gas pressure capsule which powers the jet injection and which also automatically resets the injection device during an injection in order to prepare it for a subsequent injection. A multi-function component of the device is effective to place it in a safe condition allowing the device to be prepared for a next injection, and to place the device in a ready condition for allowing a jet injection to be conducted by use of the device.

19 Claims, 4 Drawing Sheets

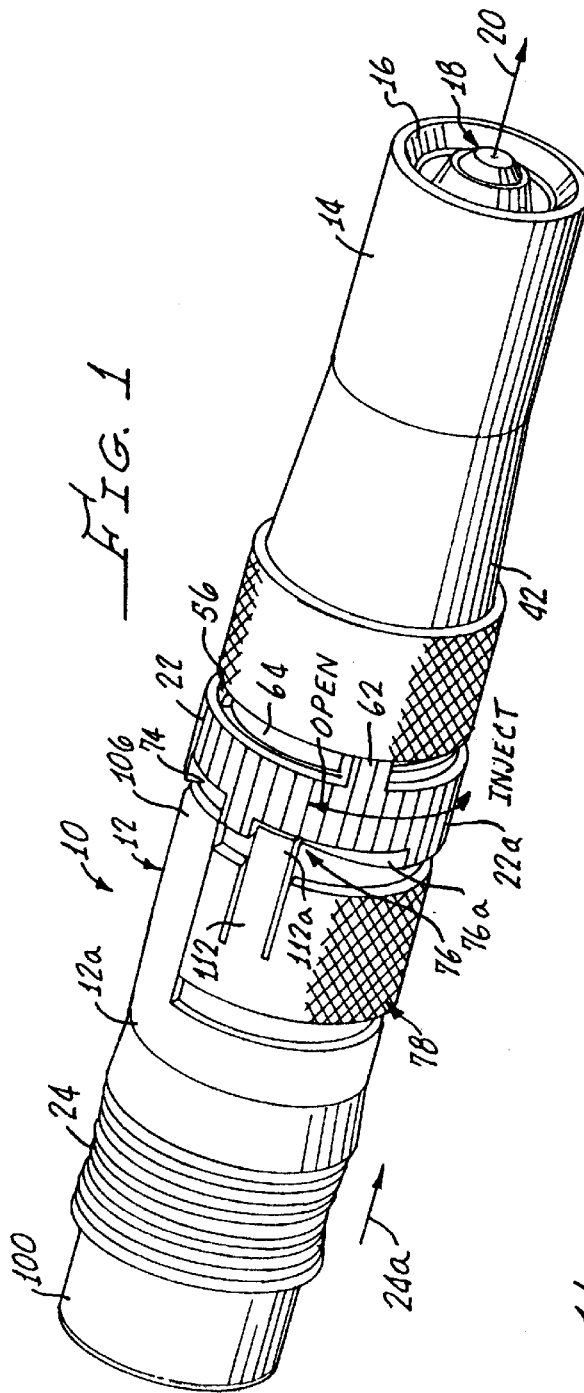
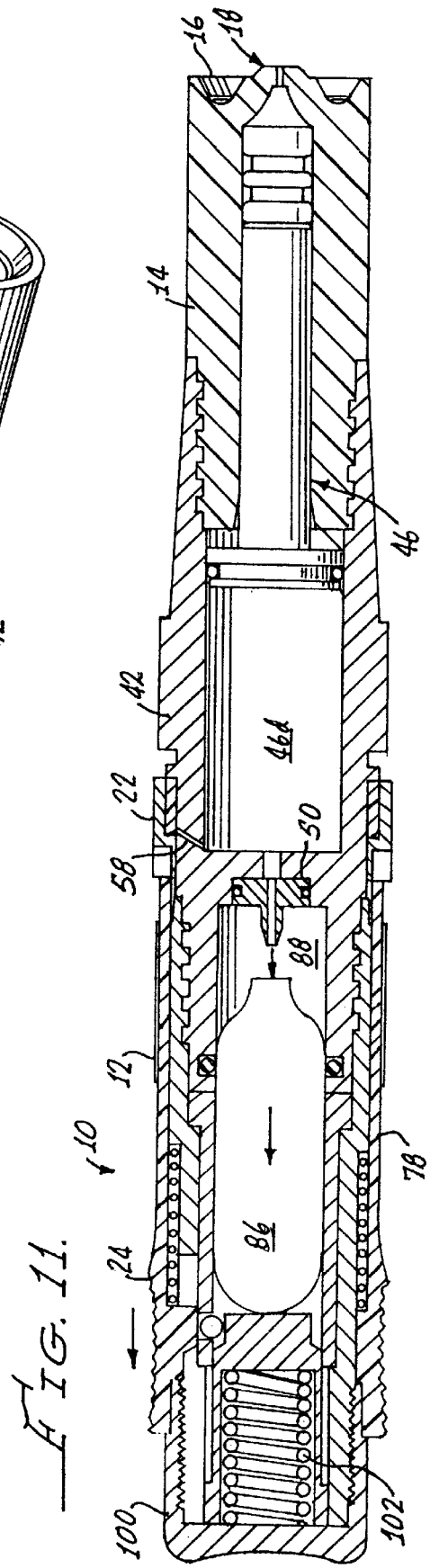

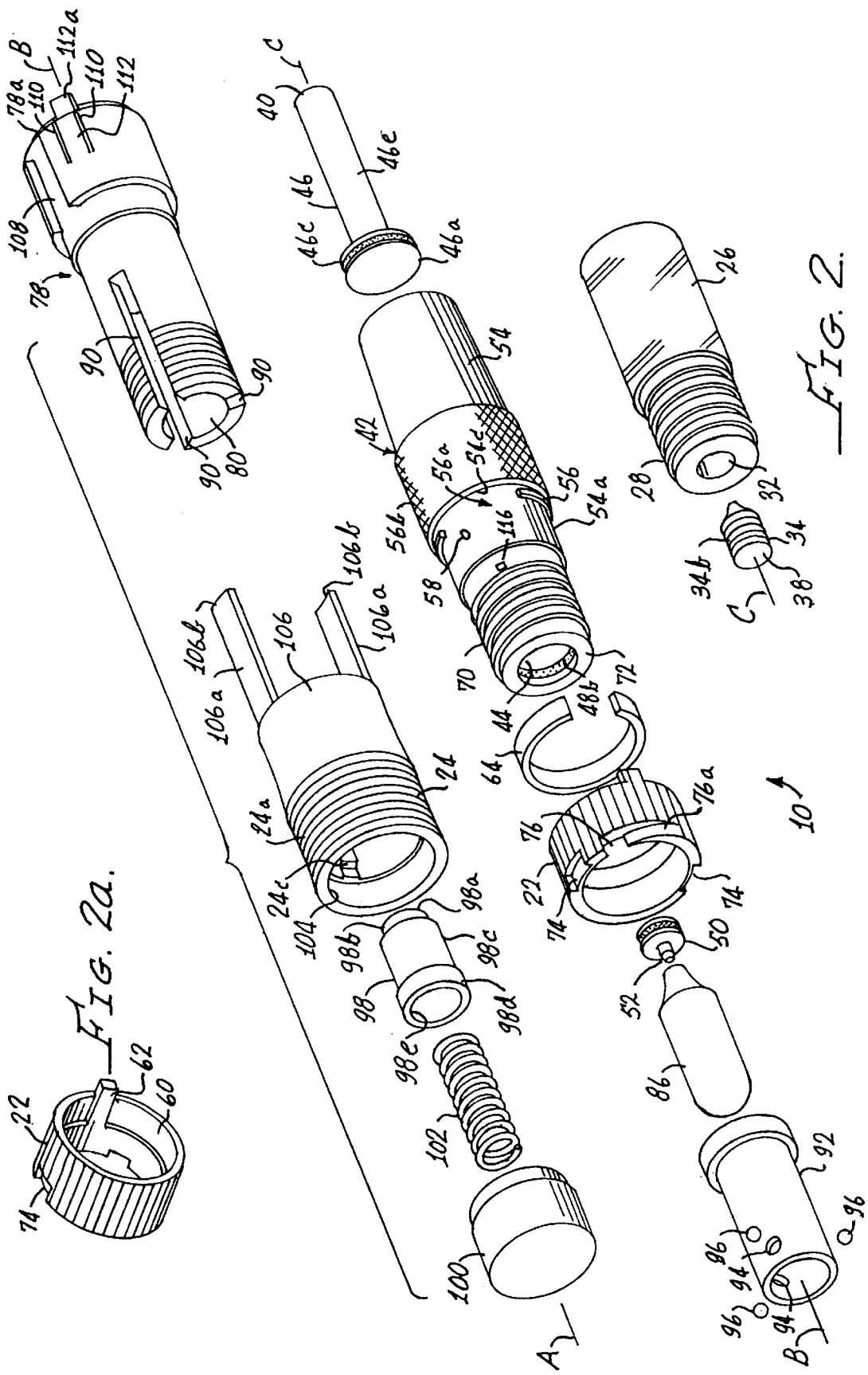

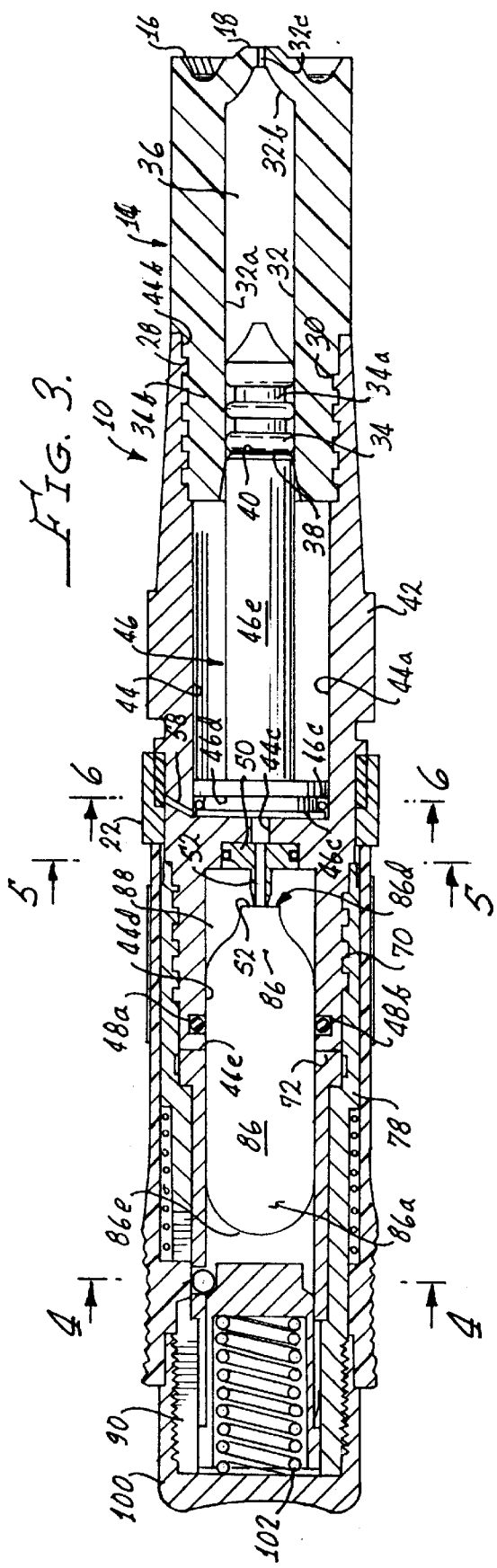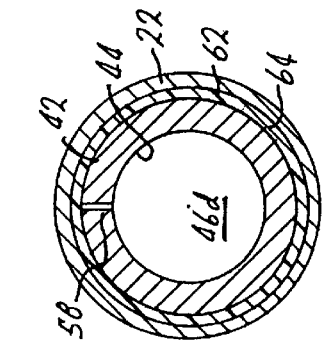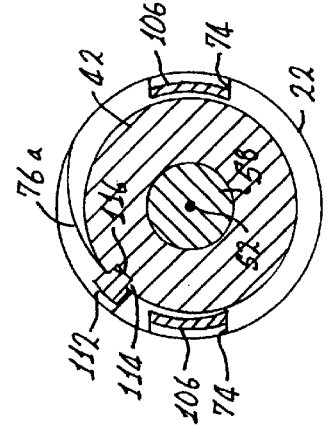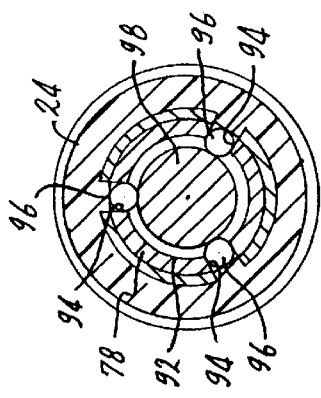

NGAS POWERED SELF-RESETTING NEEDLE-LESS HYPODERMIC JET INJECTION APPARATUS AND METHOD

BACKGROUND OF THE INVENTION

1. Field of the Invention

The present invention relates generally to a needle-less or needle-free hypodermic injection device, and particularly to such an injection device with a hand-held injector device carrying an drug cartridge pre-filled with injectable medication, a sealed cylinder of pressurized gas, a discharge mechanism for penetrating the gas cylinder, and a trigger device for releasing the discharge mechanism. The trigger device releases the discharge mechanism to penetrate the gas cylinder, which drives a piston of the drug cartridge to effect a hypodermic jet injection. The gas cylinder is also movable to automatically re-set the discharge mechanism.

2. Related Technology

Needle-less or needle-free hypodermic jet injection devices have been in commercial use for over 40 years. A number of these devices have used pressurized gas to power a hypodermic jet injection. The related technology includes a number of teachings for gas-powered injection devices, including: U.S. Pat. No. 4,596,556, issued Jun. 24, 1986 to J. Thomas Morrow, et al.; U.S. Pat. No. 4,913,699; issued Apr. 3, 1990 to James S. Parsons; and U.S. Pat. No. 5,730,723, issued Mar. 24, 1998, to Thomas P. Castellano, et al. WIPO publication WO 97/37705 also discloses a gas powered disposable needle-less hypodermic jet injector.

The Morrow, et. al. '556 patent is believed to teach a durable hypodermic jet injection device in which a housing receives a shell or cartridge having a bore leading to a discharge aperture. Within the bore is received both a plunger sealingly engaging the bore, and a pressurized gas cylinder which rests against the plunger. The injection device includes a ram which has a penetrating tip confronting a penetrable wall section and seal of the gas cylinder, and a discharge mechanism for driving the ram through the penetrable wall section of the gas cylinder when a trigger device is released. Discharge of the pressurized gas from the cylinder drives the plunger to effect a jet injection, and also drives the seal of the gas cylinder to effect resetting of the discharge mechanism. The shell with its plunger, and spent gas cylinder, is discarded after an injection; and a new shell pre-filled with medication and with a new gas cylinder is used for each injection.

The Parsons '699 patent is believed to teach a single-use jet injector which is totally discarded after one use. This injector is believed to have a body with a pair of gas chambers separated by a breakable valve. One of the gas chambers contains a pressurized gas, while the other chamber is sealingly bounded by a piston which drives a plunger. The plunger sealingly bounds a chamber into which a dose of medication is loaded by the user before the injection. This medication dose chamber leads to an injection orifice so that when the valve is broken, the piston and plunger are moved by pressurized gas communicated to the second chamber, and the plunger drives the medication forcefully out of the injection orifice to form an injection jet. After a single use, the device is discarded.

The Castellano '723 patent, which was issued in 1998 and which does not cite the earlier Parsons '699 patent, is believed to teach substantially the same subject matter as Parsons et al.

WIPO publication WO 97/37705 published pursuant to a Patent Cooperation Treaty (PCT) application for joint inventors Terence Weston and Pixey Thomlea, is believed to disclose a disposable hypodermic jet injector in which the device is powered by a gas pressure spring of the type common in the tool and die art as a substitute for the conventional metal spring ejector pin. In the Weston device, the ram of the gas pressure spring is held in a contracted position by a trigger mechanism. When the trigger mechanism is released, the gas pressure spring is supposed to expand and drive a piston sealingly received in a bore and leading to a fine-dimension orifice in order to produce a jet hypodermic injection from liquid held in the bore ahead of the piston. The Weston device is thought to have several deficiencies: such as difficult and costly manufacturing and sterilization processes, because pressurized gas and a drug dose need to be contained in the same package. including a possible inability to endure long-term storage while still retaining the gas pressure in the gas spring to power an injection, and also the medication integrity. In other words, the gas pressure spring of the Weston device contains only a small quantity of gas, and depends upon the sealing relationship of the ram of this spring with a cylinder within which the ram is movably and sealingly received in order to retain this gas pressure. Even a small amount of gas leakage over time will be enough to render this injector inoperative.

SUMMARY OF THE INVENTION

In view of the above, it is desirable and is an object for this invention to provide a needleless hypodermic jet injection device which reduces the severity of or avoids one or more of the limitations of the conventional technology.

Thus, it is an object of this invention to provide a needle-free gas-powered hypodermic jet injector utilizing a pressurized gas source which is hermetically sealed until the moment of injection. This gas source is stored apart from the injector until the injector is prepared for an injection.

Further, an object of this invention is to provide such a gas powered injector in which a disposable pressurized gas capsule provides gas pressure to operate the device, which capsule is manufactured by conventional means, and in which the body of the capsule is used in cooperation with durable structure of the injector to define a gas pressure chamber into which gas from the capsule is admitted following an injection. This gas pressure is used to act on the body of the capsule itself in order to movably reset the injector for its next operation.

Still further, an object of the present invention is to provide such a gas powered injector in which, following an injection, the injection gas pressure which has just operated the device is not allowed to vent uncontrollably to ambient, but is instead substantially contained until a user of the device chooses to allow venting of this gas. Further, when the user of the device does choose to vent the contained pressurized gas, the device performs this venting in a controlled fashion that will not startle nor injure the user.

Additionally, an object for this invention is to provide such an injection device having a multi-function component which alternatively places the injector in a safe condition or allows the trigger of the injector to be activated to perform an injection; which alternatively contains the gas from the injection capsule after an injection or allows it to be controllably vented; and which also alternatively retains the body parts of the injector united together, or allows these body parts to be separated so that the injector can be prepared for its next use to effect a hypodermic jet injection.

Accordingly, needle-less hypodermic jet injection system embodying this invention includes, for example: a needleless hypodermic jet injection device comprising: a hand piece assembly having a body for holding a drug injection cartridge with medication cylinder, injection nozzle, and drug-injection piston; the hand piece assembly defining a first bore within the body for movably receiving a gas-power piston, a gas power piston movably received in the bore and having a ram portion extending into the drug injection cartridge to abut with the drug-injection piston, the body and gas-power piston cooperating to define a first variable-volume chamber in the first bore; the body also defining an elongate second bore in gas communication with the first bore and separated therefrom by a center wall portion of the body, the body carrying a sealing member circumscribing the second bore and disposed along the length thereof so as to be sealingly engageable with a cylindrical gas capsule when the capsule is received into the second bore, the gas capsule having a penetrable wall section disposed toward the center wall, and the sealing member cooperating with the gas capsule to define a second variable-volume chamber in the second bore the volume of which varies in response to movement of the gas capsule in the body relative to the center wall; the center wall carrying a penetrator disposed toward the penetrable wall section of the gas capsule, and the hand piece assembly carrying a discharge mechanism including a trigger outwardly disposed on the body and a hammer movable in the body in response to actuation of the trigger to forcefully move the gas capsule in the second bore so as to impale the gas capsule at the penetrable wall section thereof upon the penetrator and to communicate pressurized gas to the first chamber; whereby, the pressurized gas in the first chamber drives the gas-power piston to effect a hypodermic jet injection from the drug injection cartridge, and pressurized gas communicated from the gas capsule into the second chamber moves the gas capsule sealingly relative to the sealing member to push back the hammer and reset the trigger.

Additional objects and advantages of this invention will appear from a reading of the following detailed description of a single exemplary preferred embodiment, taken in conjunction with the appended drawing Figures, in which the same reference numeral is used throughout the several views to indicate the same feature, or features which are analogous in structure or function.

BRIEF DESCRIPTION OF THE DRAWING FIGURES

FIG. 1 provides a perspective view of a needle-less hypodermic jet injector device along with a pre-filled drug cartridge preparatory to administering an injection;

FIG. 2 is a exploded perspective view of the needle-less jet injector device and drug cartridge seen in FIG. 1, along with a pressurized gas cylinder which is received into the injection device;

FIG. 2a provides a perspective view of a component of the device seen in FIG. 2, but is taken from the side opposite to that seen in FIG. 2;

FIG. 3 provides a longitudinal cross sectional view through the needle-less hypodermic jet injection device of FIG. 1, and shows the device in a condition preparatory to administering an injection;

FIGS. 4, 5, and 6 are transverse cross sectional views taken at the indicated lines of FIG. 3;

FIG. 7 provides a cross sectional view similar to that of FIG. 3, but shows the device during an injection;

FIGS. 8, 9, and 10 are transverse cross sectional views similar to FIGS. 4, 5, and 6, respectively, and are taken at the indicated lines of FIG. 7. FIGS. 9 and 10 show the device at a time after an injection during which a user of the device is preparing it for a next-subsequent injection; and FIG. 11 provides a cross sectional view similar to that of FIGS. 3 and 7, but shows the device at the completion of an injection cycle preparatory to the user renewing disposable elements of the device.

DETAILED DESCRIPTION OF AN EXEMPLARY PREFERRED EMBODIMENT OF THE INVENTION

An overview

Figure 7:
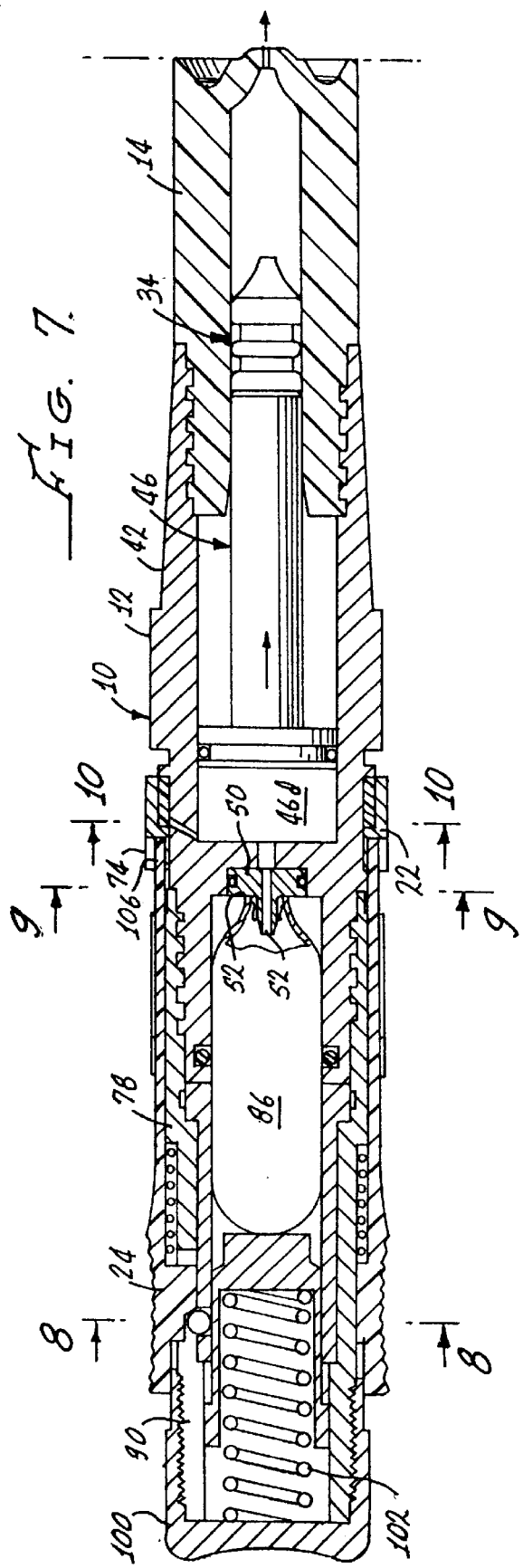

Viewing FIG. 1, a needle-free, hypodermic jet injector device 10 is shown preparatory to its use in administering an injection. The device 10 includes a hand piece assembly 12 with a body 12a which carries a pre-filled drug injection cartridge 14. The word "drug" as used herein is intended to encompass, for example, and without limitation, any medication, pharmaceutical, therapeutic, vaccine, or other material which can be administered by jet injection. The pre-filled drug injection cartridge 14 has an end surface 16 at which is defined a fine-dimension orifice opening 18 from which issues a high velocity jet of medication (as is indicated by arrow 20) upon actuation of the jet injection device 10. Actuation of the jet injection device 10 is effected by a user of the device 10 by first manually rotating a multi-function safety sleeve 22 as is indicated by arrows 22a to the position seen in FIG. 1. The surface 16 is then placed against the skin of the person who is to receive the injection, and an axial pressure is applied to a trigger sleeve 24 causing this sleeve to slide forward along the body 12a, as is indicated by arrow 24a in FIG. 1. Forward movement of the trigger sleeve 24 further presses the surface 16 against the skin of the person to receive the injection, and causes the injection 20 to be effected. Simultaneously with the injection, the device 10 resets itself automatically, allowing it to be quickly prepared to make a next subsequent injection by the replacement of the used drug cartridge 14 with a new cartridge, and also the replacement of a used power capsule (which will be further described below, and which is held within the body 12a) with a new power capsule.

Turning now to FIGS. 2, 2a, and 3, in conjunction with one another, FIG. 3 shows the device 10 in the condition of FIG. 1 preparatory to giving an injection. In FIGS. 2 and 3, it is seen that the drug cartridge 14 includes a cylindrical body 26 defining an external thread section 28. This external thread 28 is threadably received by a matching internal thread section 30 of the hand piece 12. Those ordinarily skilled in the pertinent arts will understand that alternatively, the cartridge 14 can be removably attached to the hand piece body 12a by use of a bayonet type of mutual engagement. Thus, the drug cartridge 14 is in this case manually connected to and disconnected from the body 12a by respectively fully engaging and fully disengaging the thread sections 28 and 30. The body 26 defines a stepped through bore 32 having a larger diameter portion 32a which extends substantially the length of the body 26. Adjacent to the forward end of the body 26 (i.e., at the end defining surface 16), the bore 32 includes a transition section 32b, which leads to an exceedingly fine-dimension injection orifice bore section 32c (the external opening of which was indicated with the arrowed numeral 18 in FIG. 1). Hereinafter, the injection orifice is referred to with numeral 18. The fine-dimension orifice 18 is a part of bore 32 (i.e., part 32c), but is so small that the transition section 32b effectively defines an end wall for the bore section 32a. Sealingly and movably received in the bore section 32a is a resilient piston member 34. This piston member defines multiple grooves 34a interdigitated with sealing ribs or lands 34b. The sealing ribs 34b sealingly and movingly engages the bore 32a of the body 26.

The piston member 34 and body 26 cooperatively define a medication chamber 36 communicating outwardly of the cartridge 14 via the injection orifice 18. Prior to its use to effect an injection, the orifice 18 of each fresh and pre-filled drug cartridge will ordinarily be sealed by a peel-off type of sealing membrane, which may be formed, for example, of foil or of a polymer/paper laminate. Such peel-off seals are conventional and well known, and for this reason, the seal formerly on cartridge 14 in FIG. 3 is not shown in the drawing Figures. Further considering the cartridge 14, it is seen that the piston member 32 defines a bluff or featureless back surface 38 confronting the opening of bore 34 on body 26. This surface 38 is abutted by an end surface 40 in an injection ram of the hand piece 12 (which injection ram will be further described below). The injection ram will be understood as effective during a jet injection to forcefully move the piston 34 inwardly of the bore section 32a toward abutment with the effective end wall of this bore at transition bore section 32b. Once this piston member 34 is moved in this way inwardly of the bore 32, it has no features that would allow it to be grasped and retracted toward its position seen in FIG. 3. Thus, it will be appreciated that the cartridge 14 is a pre-filled, single-use cartridge; and the consumer who uses the device 10 will have no way of refilling the cartridge 14, and this cartridge cannot be used more than once.

Hand piece assembly 12

Considering now the hand piece assembly 12 in greater detail, it is seen that the body 12a generally is formed of two main cooperative tubular sections which are threadably engaged with one another to form the hand piece assembly 12. A forward tubular body section 42 defines a stepped through bore 44, a forward portion 44a of which opens at 44b forwardly on the body 12, and which inwardly of this bore opening 44a defines the internal thread section 30 for threadably receiving the drug cartridge 14. Sealingly and movably received in the bore portion 44a is a stepped injection piston member 46. A larger diameter portion 46a of this piston member defines a groove 46b carrying a seal member 46c. The seal member 46c movingly engages sealingly with the bore portion 44a and bounds a gas pressure chamber 46d, which is to the left of this piston member as seen in FIG. 3. A smaller diameter portion 46e of the piston member 46 is elongate and extends in the bore 44 to also be received into the bore 32a of an drug cartridge 14 when such a cartridge is threadably engaged with the hand piece 12, as is seen in FIG. 3. The piston portion 46e defines the end surface 40 which confronts and abuts the surface 38 of the piston member 34 of an drug cartridge 14 when this cartridge is engaged with the hand piece assembly 12. Thus, the piston portion 46e provides the injection ram of the hand piece 12a and is cooperative with the drug cartridge 14.

As is seen in FIG. 3, the forward body section 42 also includes a center wall section 42a penetrated by a smaller diameter portion of the through bore 44, which bore portion is indicated with the reference numeral 44c. The bore portion 44c itself is stepped and is of two differing diameters, both of which are much smaller than the bore portion 44a, and is also much smaller than another adjacent larger diameter bore portion 44d. The bore portion 44d opens at 44e at the opposite end of the body section 42. Accordingly, the center wall section 42a effectively provides end walls for these bore portions 44a and 44d, which bore portions communicate with one another via the small diameter stepped bore portion 44c. Just inwardly of the opening 44e, the bore portion 44d defines an inwardly opening groove 48a receiving a seal member 48b. The purpose of this seal member 48b will be further described below. Received in the stepped small diameter bore portion 44c, in a somewhat larger diameter section of this bore, is a disk-shaped base member 50 having an axial penetrator spike 52 extending into the bore portion 44d. The purpose and function of this penetrator spike 52 will also be further explained below.

Considering the forward body section 42 in still greater detail, it is seen that this body section defines a stepped outer surface 54. A slightly smaller diameter portion 54a of the outer surface 54 cooperates with an adjacent larger diameter portion 54b to define a shoulder 54c. Spaced from the shoulder 54c the body section 42 defines an interrupted collar 56 extending radially outwardly to a diameter about equal to that of the portion 54b. This collar 56 defines a circumferentially extending gap 56a, and a vent hole 58 is formed within the circumferential extent of the gap 56, but is slightly spaced axially in a direction away from the collar 56 and away from shoulder 56a, and toward the end of this body section at which the bore portion 44d opens at 44e (i.e., toward the viewer of FIG. 2). As is seen in FIG. 3, the vent hole 58 communicates outwardly from bore portion 54 adjacent to the center wall 42a (i.e., from the chamber 46d) to open on the surface portion 54a.

Rotatably received on the cylindrical surface portion 54a of the body section 42 and adjacent to shoulder 54c is a tubular, rotatable, multi-function safety sleeve 22, which was very briefly described above. Attention now to FIGS. 2, 2a, 3, 5, and 6, will show that this safety sleeve 22 inwardly defines an interrupted circumferentially extending groove 60 (best seen in FIG. 2a). This groove 60 is interrupted by an axially extending key 62, which protrudes axially beyond the groove 60 so as to be received into the gap 56a of the collar 56. Thus, the sleeve 22 has a limited rotational freedom on the body section 42, which rotational freedom is determined by the extent of possible circumferential movement of the key 62 in the gap 56a. Preferably, the rotational freedom of ring 22 may be as much as about 90°, or may be less than this preferred angle. Received into the groove 60 is a resilient seal member 64. This seal member 64 is somewhat in radial compression between the sleeve 22 and the surface 54a of the body section 42 so that rotation of the sleeve 22 is not entirely free, but is resisted by friction of the seal member 64 on the surface 54a. Preferably, the seal member is formed of polytetrafluoroethylene (i.e., Teflon), so the frictional engagement of this seal with the body section 42 is not too great, but so that the seal member 64 may also sealingly engage the surface 54a. Thus, the sleeve 22 is manually movable by application of torque applied with the fingers of a user of the device 10. However, the sleeve member 22 is not at all so free moving that it will shift between its two operative positions without definite intentional action by a user of the device 10.

Figure 10:
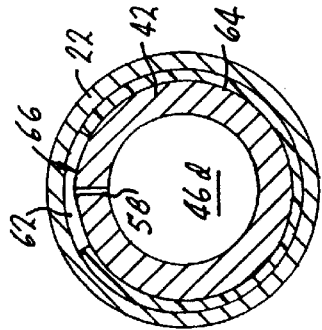
Figure 9:
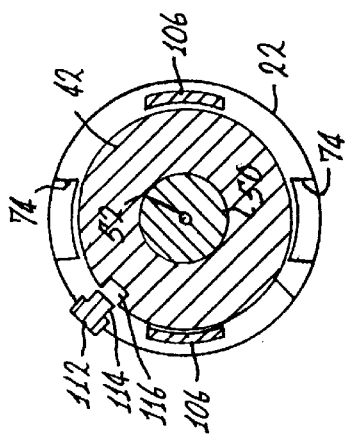
Figure 8:
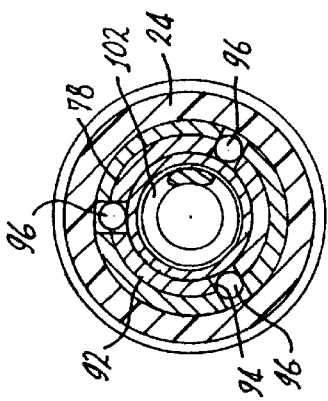

It will be seen from FIGS. 9 and 10, that when the sleeve 22 is in a "safe" rotational position with the key 62 abutting one side of the gap 56a and overlying the vent hole 58, that the chamber 46d is controllably communicated outwardly to ambient via the vent hole 58 and a fine-dimension radial gap (indicated with the arrowed reference numeral 66) is defined between the radially inner surface of the key 62 and the surface 54a of the housing section 42. Other features of the device 10 (which are described below) also allow the device 10 to be opened into two main parts. On the other hand, as is seen in FIGS. 1, 5, and 6, preparatory to the giving of an injection when the ring 22 is turned to an "inject" position defined by the key 62 abutting the other side of the gap 56a, then the seal member 64 overlies the vent hole 58, and the chamber 46d is sealingly closed from communication with the ambient. In this "inject" position of the ring 22, the features described below will be seen to lock the body of the device 10 into a single unit which cannot be opened or separated into its two main parts.

Axially beyond the surface portion 54, the body section 42 defines another shoulder 68 at which the body section 42 steps down to a smaller diameter. At this smaller diameter, the body section 42 defines an external thread section 70 leading to an axially disposed end surface 72 of the housing section 42. Viewing FIGS. 1, 2, 2a, 5, 6, 9 and 10, in greater detail, it is seen that the safety sleeve 22 has a pair of diametrically opposite notches 74 disposed axially away from the body section 46. Also, the sleeve 22 includes another gap 76 spaced circumferentially between the pair of notches 74, and which notch leads to a circumferentially-extending camming surface 76a.

Further, the body 12 also includes a tubular aft body section 78. This aft body section includes an axially disposed end surface 78a engageable with the shoulder 68, and a stepped through bore 80, which at a forward portion 80a defines an internal thread section 82 threadably engageable onto the threads 70. Aft of the thread section 82, the housing section 78 defines a step 84 engageable with the end surface 72 of the forward body section 42, and which leads to a comparatively smaller diameter bore portion 80b. This bore portion 80b, will be seen to be defined by a sub-component of the body section 78, and substantially matches the inner diameter of the bore portion 44d.

Slidably received in the bore portions 44d and 80b of the hand piece assembly 12 is a gas pressure capsule 86. This gas pressure capsule 86 includes a body 86a, having a cylindrical outer wall portion 86a'. The capsule 86 is also necked down at a forward end to provide a reduced diameter portion 86b leading to an axially disposed end surface 86c defined by a penetrable wall section 86d (the wall section being indicated by the arrowed numeral in FIG. 2). The wall section 86d confronts and is spaced slightly from the penetrator spike 52. At an opposite or aft end of the capsule 86, this capsule defines an outwardly rounded end wall 86e. It will be noted viewing FIG. 2 that the seal member 48b sealingly and movably engages the outer surface 86a' of the capsule so that the body section 42 and capsule 86 cooperatively bound a chamber 88 in the bore portion 42d adjacent to center wall 42a. That is, the capsule 86 is movable axially in the hand piece assembly 12, while the seal member 48a maintains a sealing engagement with the outer surface 86a'.

Still considering FIGS. 2 and 3, it is seen that the aft body section 78 defines three longitudinally extending slots 90 (best seen in FIG. 2), and carries a comparatively high-strength sleeve member 92, which similarly defines three holes 94 (only two of which are visible in FIG. 2) aligning circumferentially with the slots 90. The sleeve member 92 is received into the body section 78, defines a part of the bore 80b within which the capsule 86 is received, and captively receives three ball members 96, one of which is radially movably received in each one of the three holes 94. Also slidably received into the sleeve member 92 is a cylindrical hammer member 98. This hammer member 98 defines an end surface 98a which is engageable with the surface 86e of capsule 86, an annular step 98b into which the balls 96 are engaged in a first position of these balls and hammer 98 as is seen in FIG. 3, and a cylindrical outer surface 98c which captures the balls 96 in the holes 94 in a second position of the balls and hammer member 98 as is seen in FIG. 7.

Further, the hammer member 98 defines cylindrical outer surface 98d which is slightly larger in diameter than the surface 98c and is slidable in the housing section 78, and a bore 98e having an end wall 98f which is opposite to end surface 98a. An end cap 100 is threadably engaged onto the housing section 78 and closes the end of the through bore 44, as is best seen best in FIG. 2. Those ordinarily skilled in the pertinent arts will appreciate that this structure forms a ball clutch for selectively holding and releasing the hammer member 98. Between this end cap and the end wall 98f of the hammer member 98 is received a spring 102. This spring 102 is effective to drive the hammer member 98 and capsule 86 to a second position seen in FIG. 7 when the hand piece 12 is released to effect a hypodermic jet injection, as will be further explained.

Slidably received onto and about the housing section 86 is the tubular trigger sleeve 24 which defines a bore 104 for receiving the aft body section 86. This trigger sleeve 24 includes an outer surface 24a which in the exemplary embodiment is both somewhat hourglass-shaped and is circumferentially ribbed to provide good manual engagement with this trigger sleeve member by the fingers of a person using the device 10. The trigger sleeve 24 defines three longitudinally and radially extending projections 24c (a single one of which is best seen in FIGS. 3, 7, and 11), one of which is slidably received in each of the three slots 90. These projections 24c each define a respective step/ramp surface 24d, which in the first position of this trigger sleeve seen in FIG. 3 captures the balls 96 in the holes 94. Thus, the step 98b of the hammer member 98 is retained in alignment with these holes 94, and the spring 102 is under compression between the end wall 98f of the hammer member 98 and the end cap 100. In this first position of the component parts of the hand piece assembly 12 (seen in FIG. 3), the device 10 is set or cocked ready to make a hypodermic jet injection from drug cartridge 14.

Still viewing FIGS. 2 and 3, it is seen that the trigger sleeve 24 carries a diametrically opposed pair of arcuate, axially extending and elongate legs 106a. The legs 106a are slidably received in respective diametrically opposed and axially extending grooves 108 defined by the aft body section 78 (only one of which is seen in FIG. 2). Dependent upon the rotational position of the safety sleeve 22, the legs 106a may align with the notches 74 to allow the axial movement indicated by arrow 24a in FIG. 1, or may be blocked from this axial movement by confrontation and possible engagement of the legs 106a at their end surfaces 106b with this safety sleeve 22. In the rotational position of the safety sleeve 22 seen in FIGS. 5 and 6, the legs 106a align with notches 74, and the seal member 64 overlies and sealingly closes the vent hole 58. On the other hand, in the rotational position of the safety sleeve 22 seen in FIGS. 9 and 10, the legs 106a confront, are engageable with, and are prevented from axial forward movement (preventing forward movement of the trigger sleeve 24) by cooperation with the safety sleeve 22, while the key 62 aligns with vent hole 58 and defines gap 66 to controllably vent chamber 46d to ambient.

Further, it is seen in FIG. 2 that the aft body section 78 defines a pair of axially extending and closely circumferentially spaced apart slots 110 between which the aft body section 78 defines a somewhat thin, flexible, and resilient tongue portion 112. As is seen in FIGS. 2, 5, and 6, this tongue portion 112 overlies the external thread portion 70 of the forward body section 42, carries a radially inwardly extending key or projection pin 114, and also has an axially protruding end portion 112a which protrudes axially beyond the end 78a of body section 78 to be received into notch 76 of the safety sleeve 22. When the body sections 42 and 78 are fully threaded together as is seen in FIGS. 1, 3, 7, and 11, the tongue 112 aligns with a radially extending keyway 116 (best seen in FIGS. 2 and 9) defined by body section 42, so that the key 114 is received into this keyway 116 to lock the body sections 42 and 78 together. As the body sections 42 and 78 are threaded together, the tongue 112 and key 114 ride over the thread 70 to be received on surface portion 54a of the body section 42. Subsequently, the key 114 drops into the keyway 116 due to the resilience of tongue 112. Thus, when the key 114 is received into keyway 116, the body sections 42 and 78 cannot be unthreaded from one another.

However, it is to be noted that in the same condition and relative position of the body sections 42 and 78 described immediately above, the protruding end portion 112a is received into notch 76 (as is seen in FIG. 1), and is confronted by cam surface 76a of the safety sleeve 22. Thus, a user of the device 10 may relatively rotate safety sleeve 24 away from alignment of notches 74 with the ends of legs 106a (FIGS. 5 and 6), and at the same time lift tongue 112 slightly so that key 114 is lifted out of keyway 116 (FIGS. 9 and 10), allowing the body sections 42 and 78 subsequently to be unthreaded from one another. This same rotational relative movement of safety sleeve 22 on body section 42 aligns the key 62 with vent hole 58 (FIG. 10) so that the chamber 46d is vented to ambient in preparation for opening of the hand piece 12 by mutual unthreading and separation of the body sections 42 and 78.

Having observed the structure of the device 10, and its hand piece 12, attention may now be directed to its use. Viewing FIGS. 1, 3, and 4–6, once again, it will be recalled that the user places the device 10 in this condition by rotating the safety sleeve 24 on the body 12a to a position in which the notches 74 align with the legs 106 (FIG. 1). The user will have previously placed a fresh drug cartridge 14 on the hand piece 12, and will have placed a charged gas capsule 86 in the bore 44. Next, the user places the device 10 with the surface 16 against the skin at the location where the injection is to be administered, and presses forward on the trigger sleeve 24 to further press the device 10 against this skin and also to move trigger sleeve 24 slightly forward (arrow 24a of FIG. 1). As is seen by comparing FIGS. 4 and 8, and FIGS. 3 and 7, when the trigger sleeve 24 is moved slightly forward, the projections 24c move axially relative to the balls 96 so that the step/ramp surfaces 24d allow the balls 96 to move outwardly slightly off the step 98b of the hammer member 98. Thus, the trigger sleeve movement 24a is effective to release the hammer member 98 to move under the force provided by spring 102 from the position of FIG. 3 to the position seen in FIG. 7. The hammer member 98 first moves a short distance by itself, and then encounters the end surface 86d of the gas capsule 86, subsequently slamming this gas capsule (at wall section 86d) onto the penetrator 52. This penetrator 52 breaks through the wall section 86d, and communicates pressurized gas from the capsule 86 into chamber 46d. In the chamber 46d, the pressurized gas is confined because vent hole 58 is sealingly closed by seal member 64. Thus, the pressurized gas in chamber 46d forcefully drives injection piston, driving ram 46e along bore 32 of the drug cartridge (viewing FIG. 7).

The ram 46e moves piston 34 forcefully and rapidly so that the medication 36 is forced at high speed from orifice 18, effecting the hypodermic jet injection indicated on FIG. 1 by the arrow 20. Simultaneously, still viewing FIG. 7, gas pressure from capsule 86 is communicated into chamber 88 and is effective to move the capsule 86 leftwardly as seen in FIG. 7 to move the hammer member 98 once again to the position seen in FIG. 3. In other words, the capsule 86 acts as a piston sealed by seal member 48b carried in body section 42, to provide a sufficient force to overcome spring 102 and to reset or re-cock the hand piece 12. Thus, when the user releases the axial triggering force on trigger sleeve 24, the hammer member 98 will be in a position to be caught once again by the balls 96 in the position of FIG. 3.

As described previously above, after the injection event the user then rotates the safety sleeve 22 to the position moving the notches 74 out of alignment with the legs 106a, which places the device 10 in a safe condition. This movement of the safety sleeve 22 also vents the pressurized gas controllably from the hand piece 12 via vent hole 58 and gap 66. Simultaneously, the key 114 is raised out of keyway 116, so that the body sections 42 and 78 can be unthreaded from one another. When the user does so unthread these body sections, a new gas pressure capsule is placed by the user in bore 44 and the housing sections are threaded back together. The hand piece 12 is then ready to make another injection upon the user replacing the used drug cartridge 14 with a fresh one, and rotating the safety sleeve 22 from the safe position to the inject position.

An advantage of the present invention resides in its provision of a needle-less hypodermic jet injector that is durable, simple in its construction, smaller in size, and lighter in weight than many conventional devices of this type. Further, the present invention provides such an injector that is particularly convenient and safe because the single-use components (i.e., the drug cartridge and gas capsule) are small, require relatively little materials for construction, are easily and economically manufactured, and disposal of these relatively small and inexpensive components does not represent either a significant economic or ecological burden. Additionally, the injector according to this invention is uniquely easy to use because it resets or re-cocks itself after each use in preparation for its next use. Further, the use of the device is very safe because both of its main operations (namely, discharge of the device to effect an injection, and partial disassembly of the hand piece to prepare it for its next injection) are mutually exclusive of one another, and are controlled by a safety sleeve the operation of which is intuitive for many users. Even for those users not having an immediate intuitive understanding of how the hand piece 12 functions, only a few minutes of instruction are required.

While the invention has been depicted and described by reference to a particularly preferred embodiment of the invention, such reference does not imply a limitation on the invention, and no such limitation is to be inferred. The invention is capable of considerable variation and alteration in its embodiments without departing from the scope of this invention. Accordingly, the invention is intended to be limited only by the spirit and scope of the appended claims, giving cognizance to equivalents in all respects.

I claim:

1. A needle-less hypodermic jet injection device comprising:

a hand piece assembly having a body for holding a drug injection cartridge with medication cylinder, injection nozzle, and drug-injection piston; said hand piece assembly defining a first bore within said body for movably receiving a gas-power piston, a gas power piston movably received in said bore and having a ram portion extending into said drug injection cartridge to abut with said drug-injection piston, said body and gas-power piston cooperating to define a first variable-volume chamber in said first bore;

said body also defining an elongate second bore in gas communication with said first bore and separated therefrom by a center wall portion of said body, said body carrying a sealing member circumscribing said second bore and disposed along the length thereof so as to be sealingly engageable with a cylindrical gas capsule when said capsule is received into said second bore, said gas capsule having a penetrable wall section disposed toward said center wall, and said sealing member cooperating with said gas capsule to define a second variable-volume chamber in said second bore the volume of which varies in response to movement of said gas capsule in said body relative to said center wall;

said center wall carrying a penetrator means to penetrate said penetrable wall section of said gas capsule, and said hand piece assembly carrying a discharge mechanism including a trigger outwardly disposed on said body and a hammer movable in said body in response to actuation of said trigger to forcefully move said gas capsule in said second bore so as to impale said gas capsule at said penetrable wall section thereof upon said penetrator and to communicate pressurized gas to said first chamber;

whereby, said pressurized gas in said first chamber drives said gas-power piston to effect a hypodermic jet injection from said drug injection cartridge, and pressurized gas communicated from said gas capsule into said second chamber moves said gas capsule sealingly relative to said sealing member to push back said hammer and reset said trigger.

2. The jet injection device of claim 1 wherein said body includes a cylindrical section, and said trigger is tubular and is movable axially along said cylindrical body section.

3. The jet injection device of claim 2 wherein said trigger is axially movable along said body in a direction toward said drug injection cartridge in order to effect release of said discharge mechanism, so that manual force applied to said trigger also presses said injection device against the skin of a recipient for the injection.

4. The jet injection device of claim 1 wherein said body carries a multifunction safety member manually movable rotationally between first and second positions, said trigger and multifunction safety member cooperating in a first position of said multi-function safety member to allow said trigger to move to release said discharge mechanism and actuate said hammer to effect said injection, in a second position of said multi-function safety member said member blocking movement of said trigger.

5. The injection device of claim 4 wherein said body defines a fine-dimension vent hole opening outwardly from said first chamber to ambient, so that pressurized gas is vented via said vent opening to ambient following an injection.

6. The jet injection device of claim 5 wherein said multi-function safety member in said first position thereof sealingly obstructs said vent hole to permit gas pressure in said first chamber to effect said injection.

7. The injection device of claim 6 wherein said multi-function safety member in said second position thereof overlies said vent hole and outwardly of said body defines a fine-dimension gas-dispersion gap in cooperation with said body, whereby in said second position of said safety member, pressurized gas is vented controllably from said first chamber and from said second chamber via said penetrator.

8. The injection device of claim 4 wherein said body further includes a first body section and a second body section removably securing mutually to one another to bound said second chamber, said body sections being selectively removable from one another to open said second chamber and allow removal and replacement of said gas capsule.

9. The injection device of claim 8 wherein said first and second body sections cooperatively define a latch structure securing said body sections together, and said multifunction safety member includes a feature cooperating in said second position of said safety member with said latch structure to unlatch said body sections from one another and allow said second chamber to be opened by manual removal of said body sections from one another.

10. The injection device of claim 9 wherein said first body section and said second body section each define a thread portion mutually engageable with a matching thread portion of the other of these body sections to removably secure said body sections to one another.

11. The injection device of claim 10 wherein said latch structure includes one of said first and second body sections defining a resilient tongue extending axially toward and overlying the other of these body sections, said resilient tongue distally carrying a latching key receivable into a latching keyway of the other of these body sections, and said resilient tongue including an axially extending end termination portion which is engageable by said multi-function safety member in movement of said safety member from said first position thereof toward said second position thereof to lift said resilient tongue and disengage said latching key from said latching keyway.

12. The injection device of claim 11 wherein said multi-function safety member includes a circumferentially extending camming surface engageable with said end termination portion of said tongue.

13. The injection device of claim 12 wherein said multi-function safety member is configured as a sleeve rotationally carried upon said body and rotationally movable between said first and said second positions.

14. The injection device of claim 1 wherein said discharge mechanism includes a sear for engaging and holding said hammer in a first axial position storing energy in a coil compression spring preparatory to discharge of said injector device.

15. The injection device of claim 14 wherein said discharge mechanism sear includes a groove defined on said hammer, and a ball clutch carried in said injector and circumscribing said hammer, said ball clutch having at least one ball member releasably engageable into said groove of said hammer to retain the latter in said first axial position.

16. A needle-less hypodermic jet injection device for use with a drug injection cartridge having a cylinder for receiving liquid medication, an orifice for forming the liquid into a high-velocity hypodermic injection jet, and an injection piston sealingly movable in said cylinder to displace said liquid medication via said orifice; said needle-less injection device comprising:

an injector hand piece including an injection piston ram defining an end abutment surface for abutting with an opposing end surface of said injection piston of said drug cartridge, said injection ram piston in response to communication of pressurized gas thereto forcefully driving the injection piston to form an injection jet of liquid medication held in said cylinder of said drug cartridge;

said injection device including a body defining a pair of bores one of which sealingly and movably receives said injection ram piston, and the other of which sealingly and movably receives a pressurized gas capsule, a penetrator confronting a penetrable wall section of said pressurized gas capsule, and a hammer movable in said body to impale said pressurized gas capsule upon said penetrator, a resilient member for driving said hammer to a position impaling said pressurized gas capsule upon said penetrator, and a trigger device for releasing said hammer to be moved by said resilient member;

said body cooperating with said pressurized gas capsule to define a chamber receiving pressurized gas from said capsule, and communication of pressurized gas from said capsule to said chamber moving said pressurized gas capsule to retract said hammer to store energy in said resilient member preparatory to a next subsequent release of said hammer member.

17. A method of operating a needle-less hypodermic jet injection device using an injection cartridge having a cylinder for receiving liquid medication, an orifice for forming the liquid into a high-velocity hypodermic injection jet, and an injection piston movable sealingly in said cylinder to displace said liquid medication via said orifice; said method including steps of:

providing said device with a body defining a bore therein into which is sealingly and movably received a pressurized gas capsule;

utilizing said body and said pressurized gas capsule to define a variable-volume chamber; and utilizing communication of pressurized gas from said pressurized gas capsule into said variable-volume chamber to move said pressurized gas capsule in order to movably prepare said jet injection device for a next successive injection.

18. The method of operating a needle-less injection device of claim 17 further including the step of utilizing a resilient member to drive a hammer impaling said pressurized gas capsule at a penetrable wall section thereof on a penetrator carried in said body.

19. The method of operating a needle-free injection device of claim 17 further including the step of utilizing pressurized gas communicated from said pressurized gas capsule to drive a piston moving said injection piston in said cylinder to displace said liquid medication via said orifice and thus to effect said hypodermic jet injection, substantially simultaneously with movement of said gas capsule relative to said body to thereby store actuation energy in said resilient member.

* * * * *